United States Patent
Dickinson et al.

(10) Patent No.: US 8,470,008 B2
(45) Date of Patent: Jun. 25, 2013

(54) MODULAR FASTENER ASSEMBLIES FOR SPINAL STABILIZATION SYSTEMS AND METHODS

(75) Inventors: Charles A. Dickinson, Millington, TN (US); Douglas Neil Baker, Collierville, TN (US); Marco Dagoberto Capote, Memphis, TN (US)

(73) Assignee: Warsaw Othropedic, Inc., Warsaw, IN (US)

( * ) Notice: Subject to any disclaimer, the term of this patent is extended or adjusted under 35 U.S.C. 154(b) by 1970 days.

(21) Appl. No.: 11/365,732

(22) Filed: Mar. 1, 2006

(65) Prior Publication Data

US 2007/0233072 A1    Oct. 4, 2007

(51) Int. Cl.
*A61B 17/04*    (2006.01)
*A61B 17/84*    (2006.01)
*A61F 2/08*    (2006.01)

(52) U.S. Cl.
USPC ........................................................ 606/300

(58) Field of Classification Search
USPC ......... 606/71, 60, 69, 86, 246, 247, 280–289, 606/264–279, 907, 908, 910, 300–308, 315–320; 623/17.11–17.16, 23.44, 23.46, 623/23.49
See application file for complete search history.

(56) References Cited

U.S. PATENT DOCUMENTS

| | | | |
|---|---|---|---|
| 5,520,690 A | 5/1996 | Errico et al. | |
| 5,628,740 A | 5/1997 | Mullane | |
| 5,733,285 A | 3/1998 | Errico et al. | |
| 5,735,899 A * | 4/1998 | Schwartz et al. | 606/261 |
| 5,800,435 A | 9/1998 | Errico et al. | |
| 5,997,539 A | 12/1999 | Errico et al. | |
| 6,368,321 B1 | 4/2002 | Jackson | |
| 6,623,485 B2 | 9/2003 | Doubler et al. | |
| 6,733,502 B2 | 5/2004 | Altarac et al. | |
| 6,740,086 B2 * | 5/2004 | Richelsoph | 606/60 |
| 6,887,242 B2 | 5/2005 | Doubler et al. | |
| 2002/0103487 A1 | 8/2002 | Errico et al. | |
| 2004/0006342 A1* | 1/2004 | Altarac et al. | 606/61 |
| 2004/0193160 A1 | 9/2004 | Richelsoph | |
| 2004/0243126 A1 * | 12/2004 | Carbone et al. | 606/61 |
| 2005/0049589 A1 | 3/2005 | Jackson | |
| 2005/0059972 A1 | 3/2005 | Biscup | |
| 2005/0203516 A1 | 9/2005 | Biedermann et al. | |
| 2006/0084989 A1* | 4/2006 | Dickinson et al. | 606/61 |

FOREIGN PATENT DOCUMENTS

| | | |
|---|---|---|
| DE | 195 07 141 A1 | 9/1996 |
| EP | 1 364 621 A1 | 11/2003 |
| EP | 1 210 914 B1 | 5/2005 |
| WO | WO 03/059182 A1 | 7/2003 |
| WO | WO 03/068088 A1 | 8/2003 |

* cited by examiner

*Primary Examiner* — Sameh Boles (57) ABSTRACT

A fastener assembly for engaging vertebral elements has a connecting body that includes a receptacle extending between a first opening and a second opening and a fastener with a head movably supported in the receptacle. The fastener includes a vertebral engaging portion extending distally through the second opening. The fastener assembly further includes a post that has an elongated body with a proximal portion extending proximally from the first opening of the connecting body, a distal engagement end in the receptacle, and an adjusting portion extending between the proximal portion and the engagement end. The adjusting portion is movably engaged to the connecting body to position the engagement end relative to the head of the fastener to substantially fix the head in the receptacle and resist movement of the fastener with respect to the post and the connecting body.

2 Claims, 7 Drawing Sheets

MODULAR FASTENER ASSEMBLIES FOR SPINAL STABILIZATION SYSTEMS AND METHODS

BACKGROUND

The present invention relates to orthopedic devices and manner of using the same, and more particularly, but not exclusively, relates to modular fastener assemblies for spinal stabilization systems and methods.

The use of orthopedic implants to address orthopedic injuries and ailments has become commonplace. Nonetheless, there is an ever-present challenge to provide implant constructs that improve efficiency during surgery and to provide the surgeon with options for constructing an implant system that is optimized relative to the anatomical conditions and constraints encountered during surgery. Thus, there is a need for additional contributions in this area of technology.

SUMMARY

Spinal stabilization systems are provided for securing a rod, plate or other elongate connecting element along the spinal column in spinal stabilization procedures. The systems can include fastener assemblies that secure the connecting element to a vertebral body. The fastener assemblies can each include a proximal post for engagement with the connecting element.

In one embodiment, a post providing a desired characteristic can be selected during the surgical procedure from a plurality of posts having differing characteristics. The selected post is attached to a connecting body having a vertebral engaging fastener to form a fastener assembly. Other embodiments contemplate that each fastener assembly is provided with a single post. In any event, the post can be attached to a connecting body of the fastener assembly after engagement of a fastener extending distally from the connecting body with a vertebral element.

The post can engage the connecting body and is movable therein to secure the fastener in a substantially fixed orientation with respect to the connecting body and post. A series of fastener assemblies having posts can be engaged along the spinal column. The fastener assemblies can be interconnected with a connecting element positioned along the spinal column.

Further embodiments, forms, features, aspects, benefits, objects, and advantages of the present application shall become apparent from the detailed description and figures provided herewith.

DETAILED DESCRIPTION OF REPRESENTATIVE EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1A:
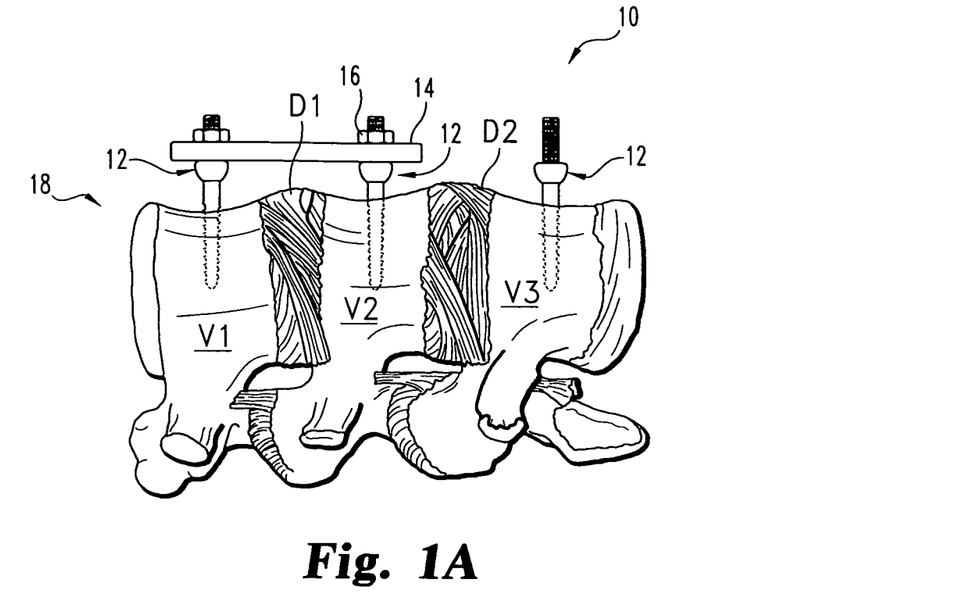
FIG. 1A is a diagrammatic elevational view of a spinal stabilization system according to one embodiment.
Figure 1B:
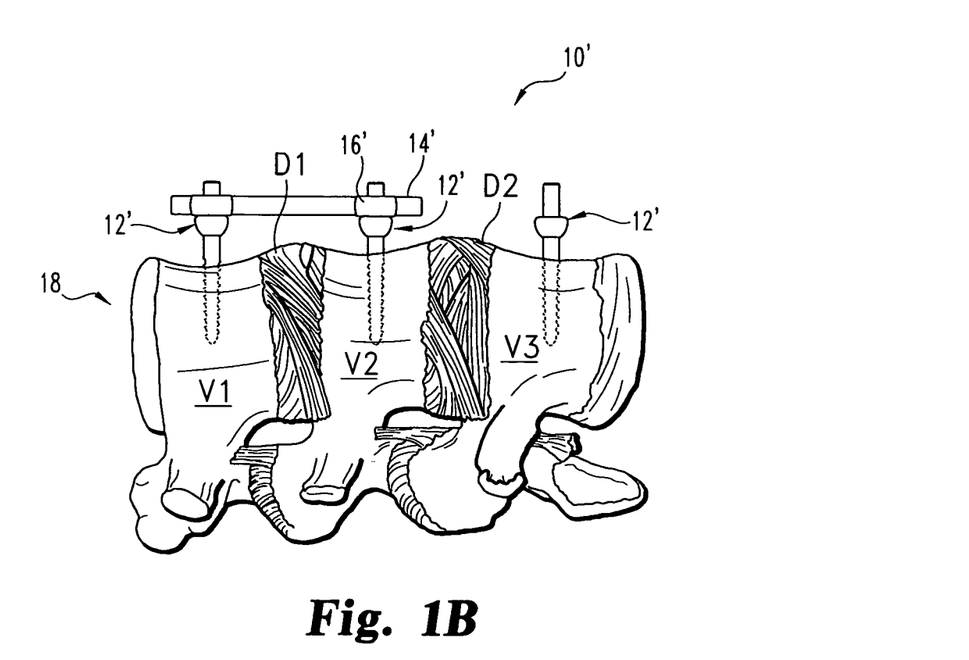
FIG. 1B is a diagrammatic elevational view of a spinal stabilization system according to another embodiment.

FIGS. 1A and 1B depict stabilizing systems 10, 10' engaged along a segment of the spinal column 18. The stabilizing systems 10, 10' can be used to assist in the healing and growth of rigid tissues by retaining vertebral bodies in a fixed or substantially fixed alignment relative to one another. The stabilizing systems 10, 10' comprise a plurality of fastener assemblies 12, 12', a connecting element 14, 14' positionable between two or more fastener assemblies 12, 12', and a plurality of engaging members 16, 16' for engaging the connecting element 14, 14' to the fastener assemblies 12, 12'.

The fastener assemblies 12, 12' are used to secure the system 10, 10' to the spinal column 18 by implanting the fastener assemblies 12, 12' into respective ones of the vertebrae V1, V2, and V3 separated by disc spaces D1 and D2. The connecting element 14, 14' engages and aligns the fastener assemblies 12, 12' with respect to one another. In one embodiment, connecting element 14 of FIG. 1A is a spinal plate. In another embodiment, connecting element 14' of FIG. 1B is a spinal rod. In FIGS. 1A and 1B, systems 10, 10' are shown engaged anteriorly to the vertebrae along spinal column 18. Systems 10, 10' can also be engaged laterally, obliquely, or posteriorly along spinal column 18. In still other embodiments, two or more stabilization systems 10, 10' can be engaged along the spinal column 18 along the same vertebrae or along differing vertebrae. Stabilization systems 10, 10' may also be employed either alone or in combination with one or more implants, fusions devices, artificial disc devices, or other device in one or more or the disc spaces D1, D2.

The connecting element 14, 14' is secured to the fastener assemblies 12, 12' by respective ones of the securing members 16, 16'. In one embodiment, engaging members 16 are threaded nuts as shown in FIG. 1A. Engaging members 16 can be threaded along a proximal post of the fastener assembly to engage connecting element 14 thereto. In another embodiment, the engaging members 16' are clamps that are slidably received about a proximal post of the fastener assemblies 12' as shown in FIG. 1B. The clamp can be secured to the proximal post in a desired position therealong, and can further include a passage (not shown) or other receptacle to receive connecting element 14' therethrough. In still other embodiments, engaging members 16, 16' may be a retaining clip, a pin, or other suitable device for engaging a connecting element 14, 14' to the proximal post of the fastener assemblies 12, 12'.

Figure 2:
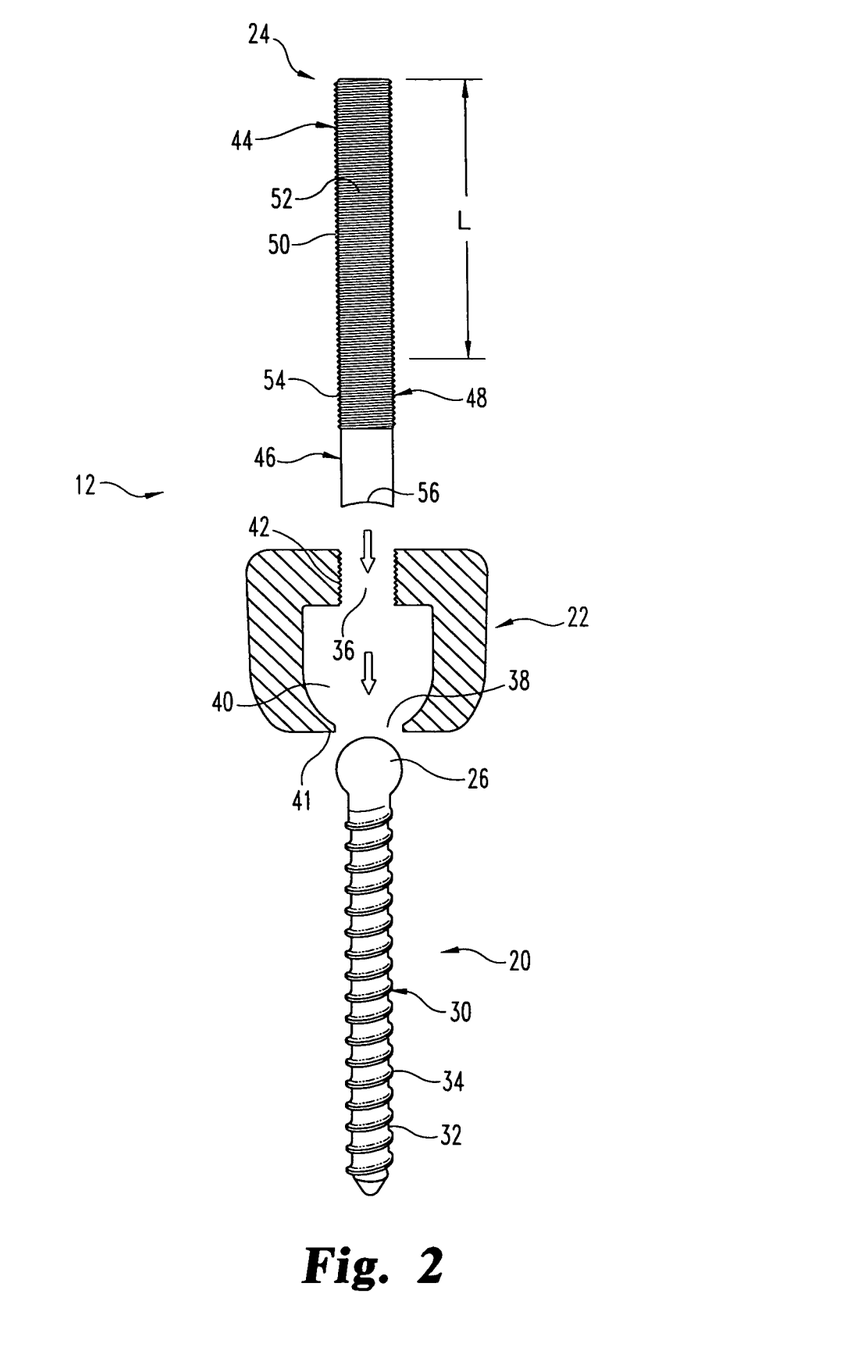
FIG. 2 is an exploded partially sectional, diagrammatic view of a fastener assembly according to one embodiment.
Figure 3A:
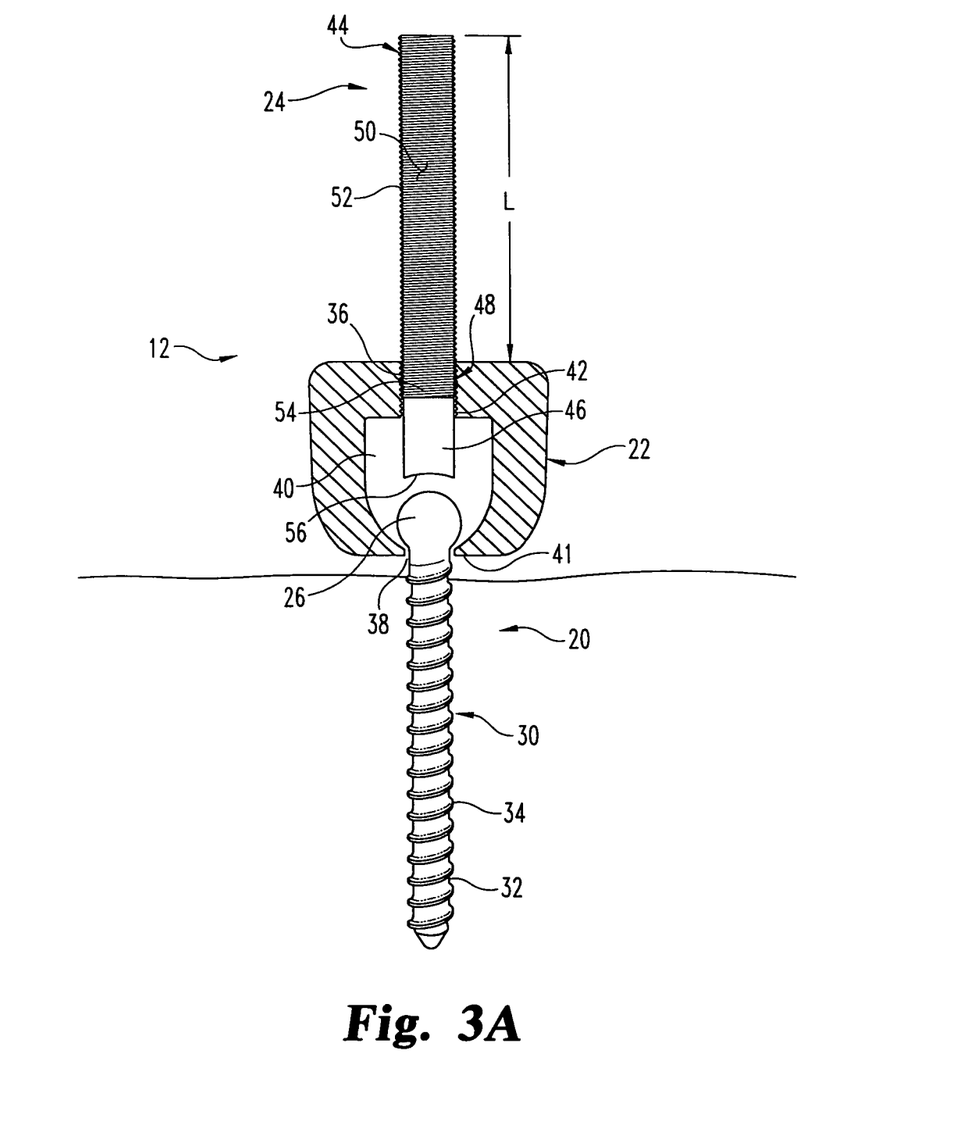
FIG. 3A is a partially sectional, diagrammatic view of the fastener assembly of FIG. 2 in a disengaged condition.
Figure 3B:
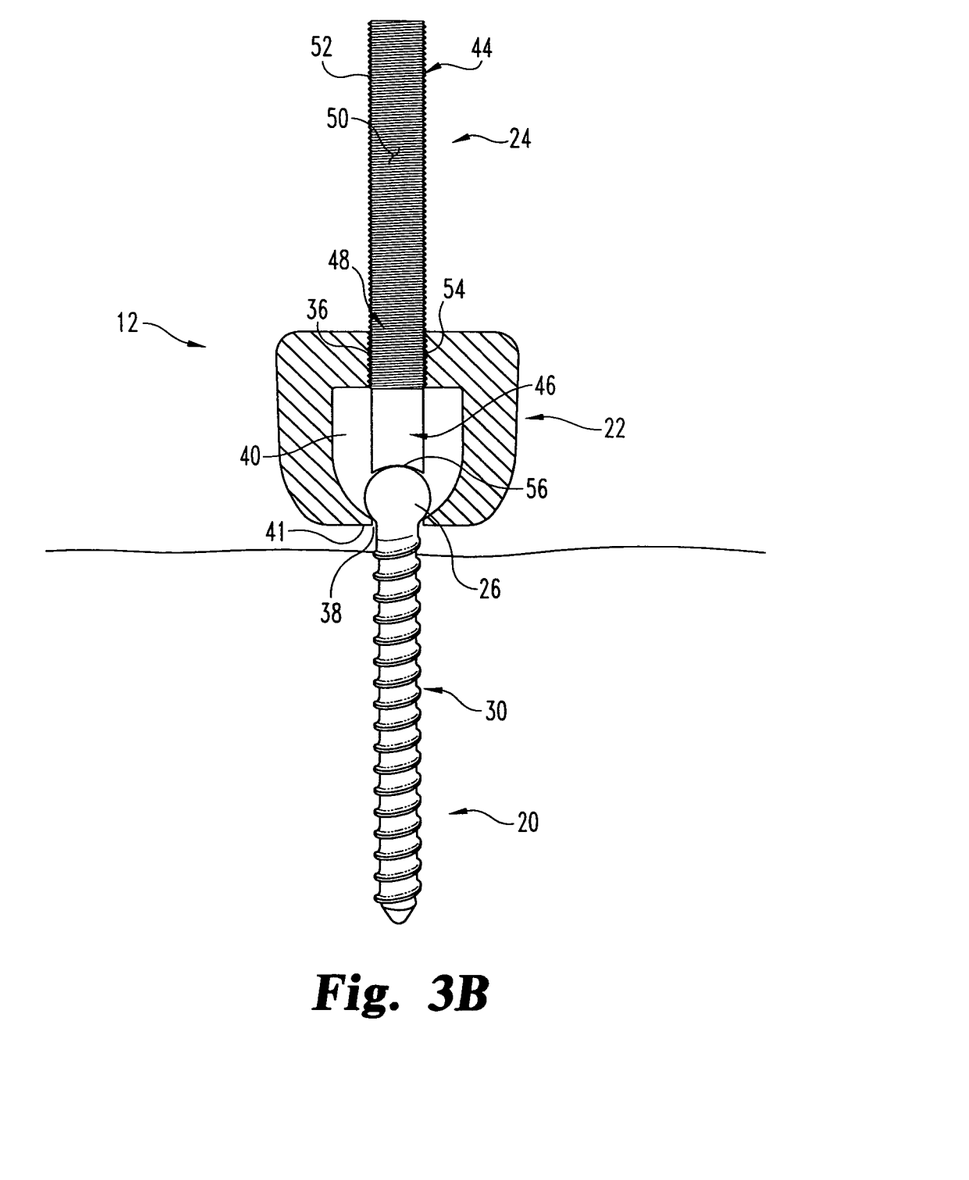
FIG. 3B is a partially sectional, diagrammatic view of the fastener assembly of FIG. 2 in an engaged condition.

FIGS. 2, 3a, and 3b illustrate one embodiment for fastener assembly 12. The fastener assembly 12 is comprised of a distal fastener 20, an intermediate connecting body 22, and a proximal post 24. The fastener 20 includes a head 26 and a vertebral engaging portion 30 that extends distally from head 26. In one embodiment, fastener 20 is a threaded bone screw. In other embodiments, fastener 20 may be a staple, a pin, a hook, or other suitable anchoring device. The head 26 can be spherically shaped and provided with a generally smooth outer surface. It should be appreciated that head 26 may have a non-spherical shape, and can include engagement structures to engage driving tools or components of fastener assembly 12.

The vertebral engaging portion 30 extends distally from head 26 and includes an elongated stem or shaft-like arrangement Vertebral engaging portion 30 can include an outer surface 32 that defines a plurality of threads 34 to engage bony tissue of the vertebral bodies V1, V2, V3. Vertebral engaging portion 30 can include at least a portion that is smaller than head 26 at least where portion 30 exits connecting body 20. The smaller portion allows fastener 20 a pivotal range of motion when head 26 is supported in connecting body 22.

Figure 4A:
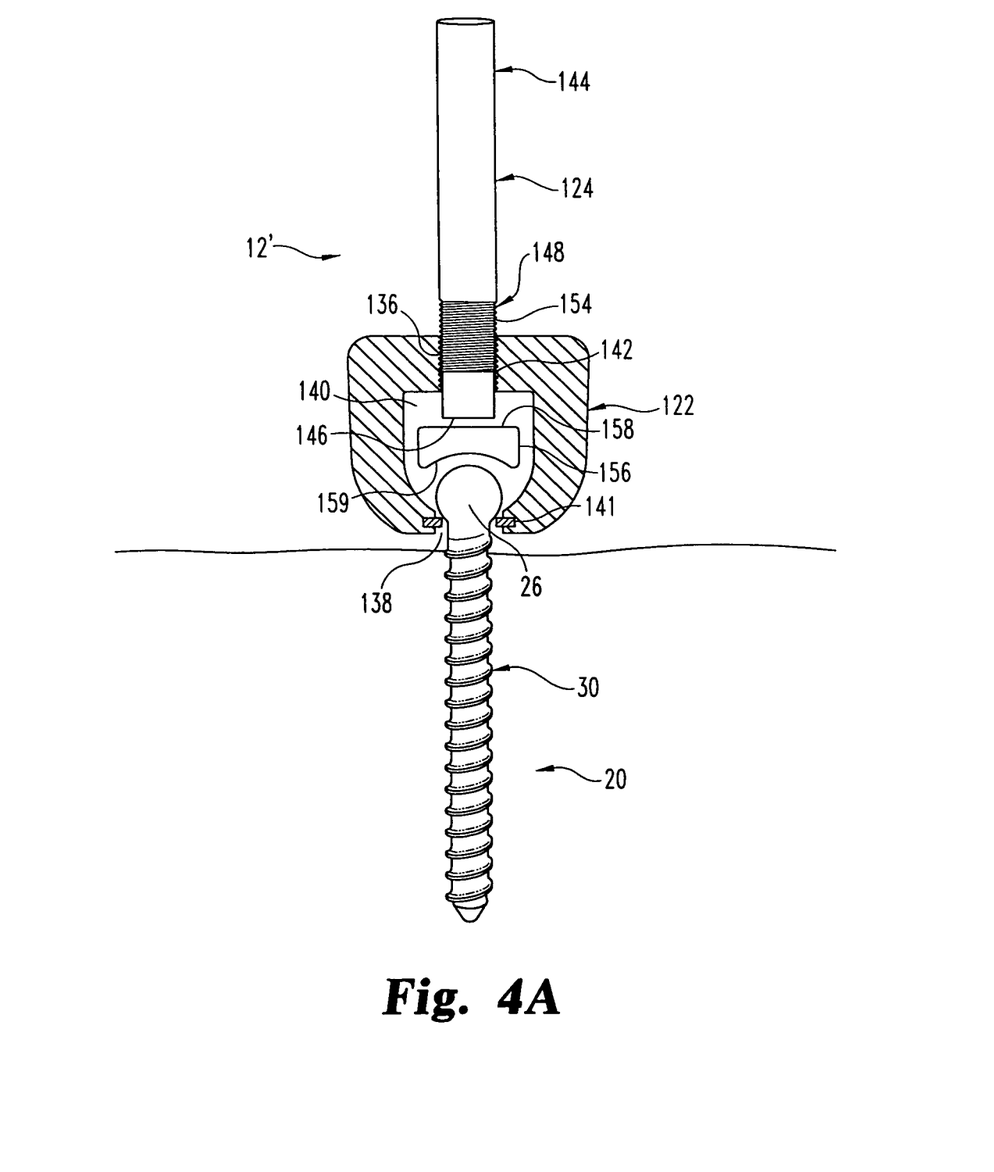
FIG. 4A is a partially sectional, diagrammatic view of a fastener assembly according to another embodiment in a disengaged condition.
Figure 4B:
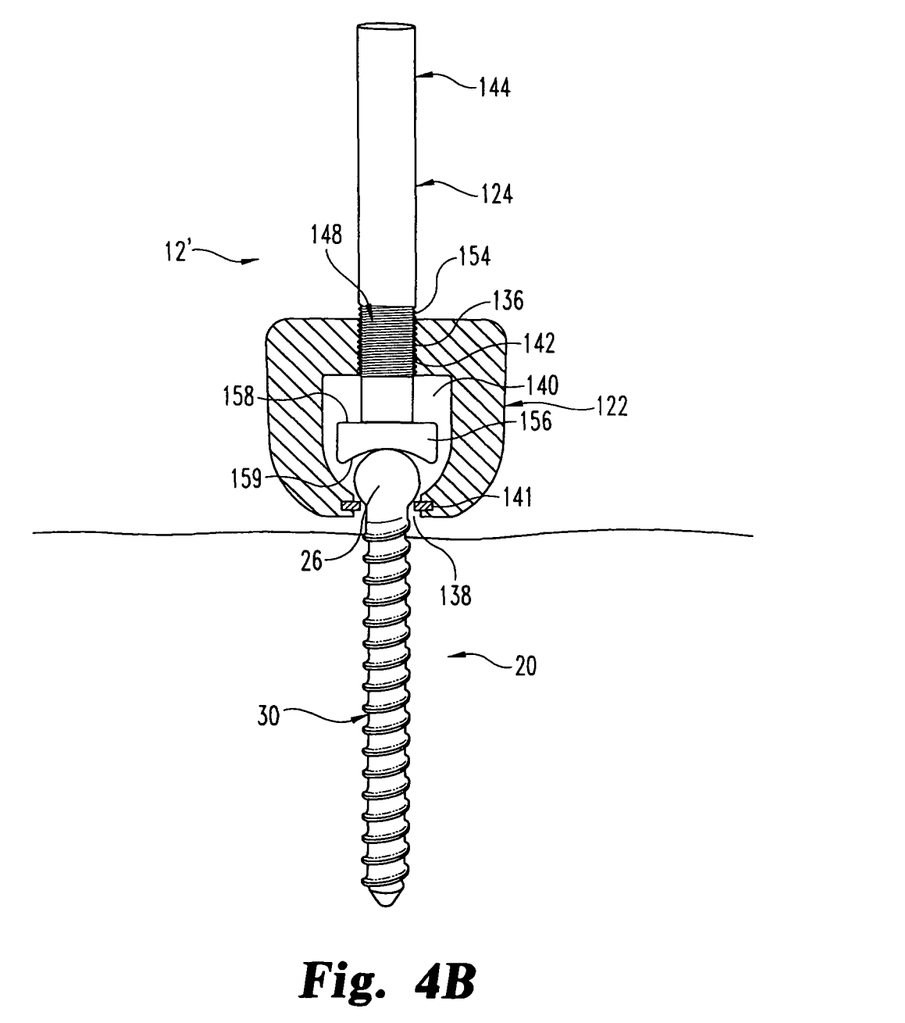
FIG. 4B is a partially sectional, diagrammatic view of the fastener assembly of FIG. 4A in an engaged condition.

The connecting body 22 extends about a receptacle 40, and includes a first, proximal opening 36, a second, distal opening 38 in communication with receptacle 40 between first opening 36 and second opening 38. The first opening 36 has threads 42 located thereabout on connecting body 22 to engage and adjust the position of post 24 within receptacle 40. The second opening 38 includes supporting member 41 that has a smaller diameter than head 26 of fastener 20 and supports head 26 within receptacle 40. The second opening 38 and supporting member 41 allow head 26 of fastener 20 to pivot about the center of supporting member 41. In one embodiment, supporting member 41 is an integral lip or flange extending about opening 38 that may be shaped to receive and support head 26 of fastener 20. In other embodiments, supporting member 41 is a retaining clip as shown in FIGS. 4A and 4B.

It should be appreciated that fastener 20 may be factory installed in connection with connecting body 22 so that the entire fastener 20 and connecting body 22 are secured together to spinal column 18. It should also be appreciated that embodiments are contemplated where connecting body 22 can be engaged to the head of fastener 20 after fastener 20 is secured to the spinal column 18.

Post 24 includes an elongated proximal portion 44, a distal engagement portion 46, and an adjusting portion 48 between the proximal portion 44 and the engagement portion 46. The proximal portion 44 can include a length L extending proximally from connecting body 22 when engaged thereto and a circular cross section transverse to length L. Post 24 may be provided in a kit or set where a plurality of posts are provided that include different lengths L, different diameters, various cross-sectional shapes or longitudinal shapes, various outer surface profiles, or other characteristic along proximal portion 44. Proximal portion 44 has an outer surface 50 that defines threads 52 extending thereabout. It should be appreciated that outer surface 50 may be also be smooth such as shown in FIGS. 4A and 4B.

Proximal portion 44 of post 24 includes threads 52 that may be engaged by connecting element 14 and/or an engaging means 16 to secure the connecting element 14 to post 24. It should be appreciated that proximal portion 44 may includes threads 52 or other structure that may be engaged by an instrument that is operable to rotate post 24 to adjust the position of distal engagement end 56 within receptacle 40 of connecting body 22. It should also be appreciated that proximal portion 44 can be configured with threads 52 or other structure that may be engaged by an instrument that can apply forces to move vertebral elements into alignment with one another.

Post 24 includes adjusting portion 48 with threads 54 that engage threads 42 about first opening 36 of connecting body 22. It should be appreciated that threads 54 may have a pitch that is the same as or that differs from those of threads 52 on proximal portion 44. The engagement of adjusting portion 48 in first opening 36 positions engagement portion 46 within receptacle 40 of connecting body 22. Adjusting portion 48 can also be configured to include threads 54 that turn in either the same or the opposite direction of threads 52 along proximal portion 44.

The engagement portion 46 includes a distal engagement end 56 that engages head 26 of fastener 20. Engagement end 56 can be shaped concave to engage the spherically shaped head 26 in a universal joint type arrangement. The longitudinal axes of post 24 and fastener 20 need not be aligned with one another to provide intimate contact between post 24 and fastener 20, allowing fastener 20 to be engaged to the vertebral element with a driving instrument that is off-axis relative to the orientation of the post 24 when it is subsequently engaged to connecting body 22 and orientated in the desired orientation. It should be appreciated that engagement end 56 may be flat, convex, or any other suitable shape.

When distal engagement portion 46 is positioned within receptacle 40 of connecting body 22 and post 24 is rotated to threadingly engaged adjustment portion 48 with connecting body 22, connecting body 22 is advanced proximally along post 24 until distal engagement end 56 engages head 26 of fastener 20. Engagement end 56 urges head 26 against supporting member 41 of connecting body 22 adjacent second opening 38, and substantially fixes fastener 20 thereagainst to preventing movement of fastener 20 with respect to connecting body 22 and post 24, as shown in FIG. 3B.

In operation, connecting body 22 and fastener 20 of fastener assembly 12 are implanted into a respective one of the vertebral elements with threads 34 on vertebral engaging portion 30 of fastener 20 engaging a vertebral element. After engagement of fastener 20 and connecting body 22, post 24 can be selected from a plurality of posts 24 having proximal portions 44 with differing characteristics. The engagement end portion 46 of the selected post 24 is inserted into connecting body 22 through first opening 36. The threads 54 of adjustment portion 48 of post 24 engage threads 42 about first opening 36 to position distal engagement end 56 within receptacle 40. As post 24 is rotated in threaded engagement with connecting body 22, connecting body 22 is displaced proximally along post 24 and distal engagement end 56 moves toward and engages head 26 of fastener 20. Distal engagement end 56 urges head 26 against supporting member 41 about second opening 38 and substantially fixes head 26 in connecting body 22 to prevent movement of fastener 20 with respect to body 22 and post 24.

With head 26 of fastener 22 substantially fixed by post 24 against the supporting member 41, the attachment of posts to other fastener assemblies along the spinal column can be completed. The other posts can be selected with proximal portions 44 that have characteristics therealong that differ from the other posts. Connecting element 14 and engaging member 16 are coupled to the fastener assemblies 12 to provide a stabilization system along a portion of the spinal column.

FIGS. 4A and 4B illustrate fastener assembly 12' according to another embodiment. The fastener assembly 12' is comprised of fastener 20, a connecting body 122, and a post 124. The connecting body 122 includes a first, proximal opening 136, a second, distal opening 138, and a receptacle 140 between first opening 136 and second opening 138 that contains a crown 156. The crown 156 includes a proximal surface 158 that engages post 124 and a distal surface 159 that engages head 26 of fastener 20. The proximal surface 158 is generally flat, while distal surface 159 is generally concave to engage the spherical surface of head 26. It should be appreciated that proximal surface 158 and distal surface 159 may be other shapes such as convex and/or include an opening or slot therethrough for passage of a driving instrument to engage head 26 of fastener 20.

The post 124 includes a proximal portion 144, a distal engagement end 146, and an adjusting portion 148 between the proximal portion 144 and engagement end 146. The engagement end 146 can be generally flat to abuttingly engage proximal surface 158 of the crown 156.

In operation, the spinal column segment 18 is accessed and prepared during a surgical procedure, connecting body 122 and fastener 20 of the fastener assembly 12' are implanted into the respective vertebrae with vertebral engaging portion 30 of the fastener 20 engaging the vertebral body to secure fastener 20 and connecting body 122 thereto. After placement of fastener 20 and connecting body 122, post 124 can be selected from a group of posts having proximal portions 144 with differing characteristics. In the illustrated embodiment, post 124 includes a proximal portion 144 with a smooth outer surface therealong. Other characteristics for selection of the desired post 124 can include the length, diameter, or other feature or combination of features desired for proximal portion 144. For example, a first length of the proximal portion 144 of the post 124 may be greater than a second length of the proximal portion of another post. Engagement end 146 of the selected post 124 is inserted into connecting body 122 through the first opening 136. The threads 154 of adjustment portion 148 engage the threads 142 about first opening 136 to position engagement end 146 within receptacle 140.

When post 124 is threadingly advanced into connecting body 122, engagement end 146 moves toward and engages crown 156 contained within receptacle 140. Engagement end 46 urges crown 156 toward head 26. Crown 156 engages head 26 and urges head 26 against supporting member 141 extending about second opening 138. Crown 156 substantially fixes head 26 against supporting member 141 to prevent movement of fastener 20 with respect to body 122 and post 124. Once head 26 of fastener 20 is substantially fixed in connecting body 122, connecting element 14' and securing member 16' can be coupled to post 124 of fastener assembly 12' and connecting with other adjacent fastener assemblies 12' or other fastener arrangements.

Figures 5, 6, 7:
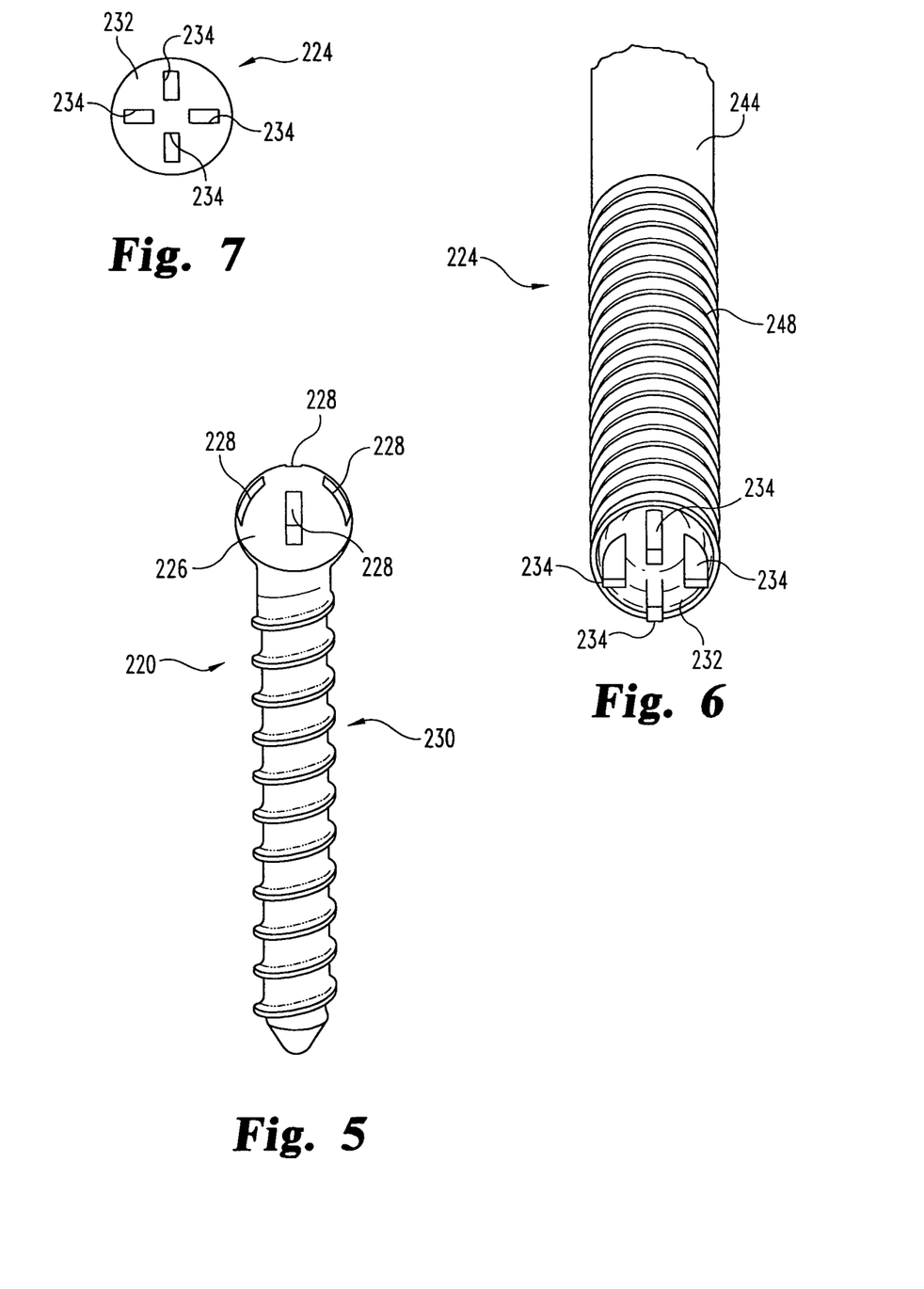
FIG. 5 is a perspective view of a fastener according to another embodiment.
FIG. 6 is a perspective view looking toward the bottom of a post engageable with the fastener of FIG. 5.
FIG. 7 is a bottom elevational view of the post of FIG. 6.

FIGS. 5, 6, and 7 illustrate components of another embodiment fastener assembly. The components include a fastener 220 and a post 224 that can be connected to one another with either of the connecting body embodiments 22, 122 discussed above. Fastener 220 includes a head 226 and a vertebral engaging portion 230 extending distally from head 226. Head 226 has at least one recessed slot 228 therein. In the illustrated embodiment, head 226 include four slots 228 spaced equally thereabout. The recessed slots 228 can be engaged by a distal engagement end 232 of post 224. Specifically, engaging end 232 includes a number of protrusions 234 spaced thereabout that can be received in slots 228 when post 224 is positioned in contact with fastener 220. It should also be appreciated that the recessed slots 228 may be engaged additionally or alternatively by an instrument used to implant fastener 220.

The post 224 includes a proximal portion 244, and an adjusting portion 248 between proximal portion 244 and the engagement end 232. Adjusting portion 248 can threadingly engage connecting body 22, 122 in the proximal opening thereof. The engagement end 232 can be shaped to conform to the outer surface profile of head 226 so that protrusions 234 securely engage the recessed slots 228 in head 226.

In operation, the connecting body and fastener 220 are implanted into and engaged to a vertebral element with vertebral engaging portion 230 of fastener 220. Post 224 can then be selected and engagement end 232 of the selected post 224 is inserted into the connecting body through the proximal opening Adjustment portion 248 of the post 224 can engage the connecting body, and post 224 advanced to position protrusions 234 on engagement end 232 into respective ones of the aligned recessed slots 228 in head 226 of fastener 220. The engagement end 232 is thus locked in position relative to fastener 220 and relative movement between the fastener 220 and post 224 is prevented.

In one embodiment, the apparatus comprises a fastener, a connecting body, and a post. The fastener includes a proximal head and a vertebral engaging portion that extends distally from the head. The connecting body defines a receptacle that extends between a first opening and a second opening. The first opening includes a plurality of threads. The head of the fastener is movably supported within the receptacle with the vertebral engaging portion extending distally through the second opening. The post has an elongated body that includes a proximal portion extending proximally from the first end of the connecting body, a distal engagement end, and an adjusting portion extending between the proximal portion and the engagement end. The adjusting portion engages the threads at the first opening of the connecting body. The engagement end is positionable in the receptacle of the connecting body relative to the head of the fastener to substantially fix the head in the connecting body adjacent the second opening of the connecting body by threadingly adjusting the adjusting portion along the first opening of the connecting body.

In still another embodiment, the apparatus comprises a fastener, a connecting body, a first post, and a second post. The fastener includes a proximal head and a vertebral engaging portion that extends distally from the head. The connecting body defines a receptacle that extends between a first opening and a second opening. The head of the fastener is movably supported within the receptacle with the vertebral engaging portion extending distally through the second opening. The first and second posts each have an elongated body that includes a proximal portion extendable proximally from the first opening of the connecting body and a distal engagement end positionable in the receptacle relative to the head of the fastener. The distal engagement end is positionable relative to the connecting body to substantially fix the head in the connecting body adjacent to the second opening and prevent movement of the fastener with respect to the post and connecting body. The proximal portions of the first and second posts can each include a characteristic that differs from the other, and the post providing the desired characteristic can be selected for engagement with the connecting body.

In a further embodiment, first and second fasteners each having a proximal head and a vertebral engaging portion extending distally from the head are secured to vertebral elements. Each fastener includes a connecting body that defines a receptacle extending between a first opening and a second opening. The connecting body movably supports the head of the fastener within the receptacle with the vertebral engaging portion extending distally through the second opening of the connecting body. First and second posts each have an elongated body that includes a proximal portion, a distal engagement end, and an adjustment portion that extends between the proximal portion and the engagement end. The engagement end of each post is positioned within the receptacle of the respective connecting body of the first and second fastener assemblies so that the adjusting portion engages the first opening of the body and the head of the fastener is engaged by the engagement end of the post to substantially fix the head relative to the connecting body adjacent the second opening to substantially prevent movement of the fastener with respect to the post and connecting body.

In yet a further embodiment, a fastener having a proximal head that is movably supported within a connecting body and a vertebral engaging portion extending distally from the head, is secured to vertebral tissue. A plurality of posts are provided that each have an elongated body that includes a proximal portion, a distal engagement end, and an adjustment portion that extends between the proximal portion and the engagement end. The proximal portion of at least two of the plurality of posts can have a characteristic that differs among the plurality of posts. One post having a desired characteristic is selected from the plurality of posts, and the adjusting portion of the selected post is engaged to the connecting body.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary.

What is claimed is:

1. An apparatus, comprising:
   a fastener having a proximal head and a vertebral engaging portion extending distally from the head;
   a connecting body defining a receptacle extending between a first opening and a second opening, the first opening having a plurality of threads, the head of the fastener being movably supported within the receptacle with the vertebral engaging portion extending distally through the second opening, the connecting body including a supporting member defining an inwardly extending flange extending about the second opening which is sized smaller than the head of the fastener to maintain the head within the receptacle; and
   a post having an elongated body including a proximal portion extending proximally from the first opening of the connecting body, a distal engagement end, and an adjusting portion between the proximal portion and the engagement end, the distal engagement end sized smaller than the first opening in the connecting body to permit insertion of the distal engagement end through the first opening and into the receptacle, the adjusting portion engaging the threads at the first opening of the connecting body and being movable therealong to move the engagement end in the receptacle distally toward the head of the fastener and into engagement with the head to substantially fix the head of the fastener in the connecting body adjacent the second opening of the body and with the head urged distally toward the inwardly extending flange by the engagement end of the post and into compressed engagement against the inwardly extending flange of the connecting body to substantially prevent movement of the fastener with respect to the post and the connecting body; and
   wherein the post includes a plurality of posts with at least one of the plurality of posts having a proximal portion with a threaded outer surface extending therealong and another of the plurality of posts having a proximal portion with a smooth outer surface extending therealong.

2. An apparatus, comprising:
   a fastener having a proximal head and a vertebral engaging portion extending distally from the head;
   a connecting body defining a receptacle extending between a first opening and a second opening, the head of the fastener being movably supported within the receptacle with the vertebral engaging portion extending distally through the second opening, the connecting body including a supporting member defining an inwardly extending flange extending about the second opening which is sized smaller than the head of the fastener to maintain the head within the receptacle;
   a first post having an elongated body including a proximal portion, an adjusting portion, and a distal engagement end, the distal engagement end sized smaller than the first opening in the connecting body to permit insertion of the distal engagement end through the first opening and into the receptacle, the adjusting portion engaged with the first opening and being movable therealong to move the engagement end distally toward the head of the fastener and into engagement with the head to substantially fix the head in the connecting body adjacent the second opening and with the head urged distally toward the inwardly extending flange by the engagement end of the post and into compressed engagement against the inwardly extending flange of the connecting body to resist movement of the fastener with respect to the first post and the connecting body with the proximal portion of the first post extending proximally from the first opening, the proximal portion of the first post having a first characteristic extending therealong; and
   a second post having an elongated body including a proximal portion, an adjusting portion, and a distal engagement end, the distal engagement end sized smaller than the first opening in the connecting body to permit insertion of the distal engagement end through the first opening and into the receptacle, the adjusting portion engaged with the first opening and being movable therealong to move the engagement end distally toward the head of the fastener and into engagement with the head to substantially fix the head in the connecting body adjacent the second opening and with the head urged distally toward the inwardly extending flange by the engagement end of the post and into compressed engagement against the inwardly extending flange of the connecting body to resist movement of the fastener with respect to the second post and the connecting body with the proximal portion of the second post extending proximally from the first opening, the proximal portion of the second post having a second characteristic extending therealong that differs from the first characteristic of the first post, wherein one of the first and second posts is selected for engagement with the connecting body; and
   wherein the first characteristic includes a smooth outer surface along the proximal portion of the first post and the second characteristic includes a threaded outer surface along the proximal portion of the second post.

\* \* \* \* \*